United States Patent
Tamura et al.

(10) Patent No.: US 6,852,867 B2
(45) Date of Patent: Feb. 8, 2005

(54) PROCESS FOR PREPARATION OF A BENZOFURAN DERIVATIVE

(75) Inventors: Kunio Tamura, Tokyo (JP); Hirohito Shimizu, Tokyo (JP); Yoshiaki Kato, Shizuoka (JP); Masahiro Shimizu, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 126 days.

(21) Appl. No.: 10/333,220

(22) PCT Filed: Jul. 19, 2001

(86) PCT No.: PCT/JP01/06296

§ 371 (c)(1),
(2), (4) Date: Jan. 21, 2003

(87) PCT Pub. No.: WO02/06263

PCT Pub. Date: Jan. 24, 2002

(65) Prior Publication Data

US 2003/0204100 A1 Oct. 30, 2003

(30) Foreign Application Priority Data

Jul. 19, 2000 (JP) ........................................ 2000-219902

(51) Int. Cl.$^7$ ............................................. C07D 307/79
(52) U.S. Cl. ...................................................... 549/462
(58) Field of Search ........................................ 549/462

(56) References Cited

U.S. PATENT DOCUMENTS 5,574,178 A 11/1996 Tamura et al.

FOREIGN PATENT DOCUMENTS

| EP | 0 650 952 A1 | 5/1995 |
| EP | 0 665 208 A1 | 8/1995 |
| JP | 6-206842 | 4/1994 |
| JP | 7-188094 A | 7/1995 |
| WO | WO 94/08930 A | 4/1994 |

OTHER PUBLICATIONS

Katritzky, A.R. et al., "The preparation of 1–17 some heteroaromatic and aromatic aldehydes", ARKIVOC, vol. 1, No. 3 (2000), p. 240–251.

Primary Examiner—Taofiq Solola
(74) Attorney, Agent, or Firm—Browdy and Neimark, P.L.L.C.

(57) ABSTRACT

An industrially useful process for producing benzofuran derivatives of formula (1):

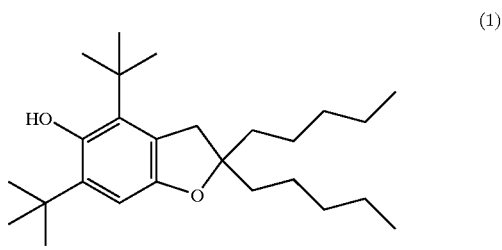

by formylating a compound of formula (2):

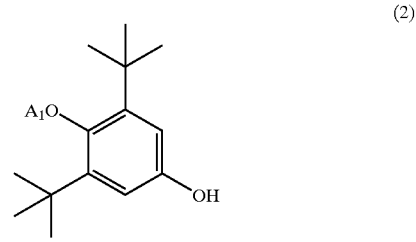

(where $A_1$ is a protective group), followed by reaction with a compound of formula (4):

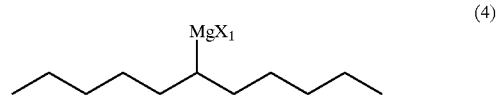

(where $X_1$ is a halogen atom), then performing a cyclizing reaction and subsequently performing a reaction for hydroxyl group deprotection.

17 Claims, No Drawings

PROCESS FOR PREPARATION OF A BENZOFURAN DERIVATIVE

This Appln is A 371 of PCT/JP01/06296 filed Jul. 19, 2001.

TECHNICAL FIELD

This invention relates to an industrially useful process for producing benzofuran derivatives.

BACKGROUND ART

Compounds represented by formula (1) set forth below are substances known as antioxidants that are useful as therapeutics of ischemic diseases such as arteriosclerosis and myocardial infarction; methods for their production are described in Japanese Patent Laid-Open No. 206842/1994, WO94/08930 and U.S. Pat. No. 5,574,178.

However, those production methods require prolonged reaction steps and involve a plurality of purification steps by column chromatography in the course of reactions and because of these and other problems, they have not necessarily been satisfactory as industrial processes for production.

DISCLOSURE OF THE INVENTION

As a result of their intensive studies, the present inventors found efficient processes for producing compounds represented by the formula (1) and completed the present invention:

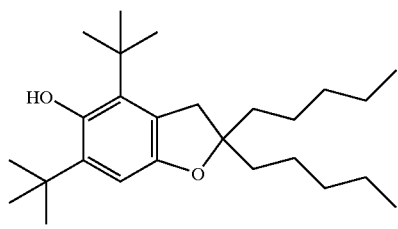

(1)

Thus, the present invention relates to industrially useful processes for producing benzofuran derivatives.

Specifically, the invention provides a process for producing a compound represented by formula (1):

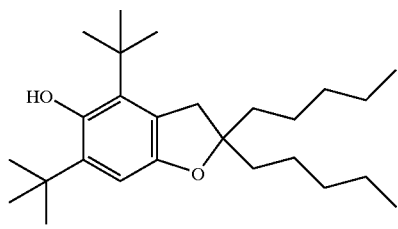

(1)

which comprises the first step of formylating a compound represented by formula (2):

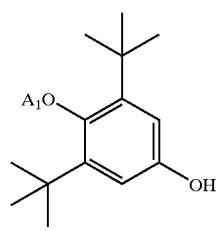

(2)

(where $A_1$ is a protective group) to give a compound represented by formula (3):

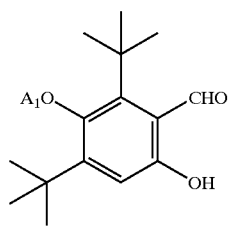

(3)

(where $A_1$ is a protective group), the third step of reacting the compound of formula (3) with a metal hydride and thereafter reacting the same with a compound represented by formula (4):

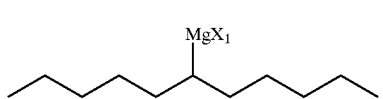

(4)

(where $X_1$ is a halogen atom) to give a compound represented by formula (5):

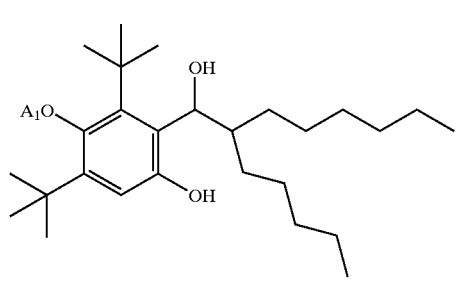

(5)

(where $A_1$ is a protective group), the fifth step of cyclizing the compound of formula (5) to give a compound represented by formula (6):

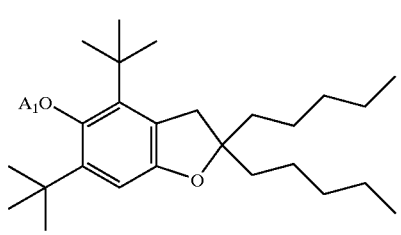

(6)

(where $A_1$ is a protective group), and the seventh step of deprotecting the compound of formula (6) to give a compound represented by formula (1):

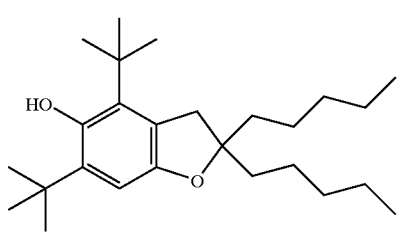

(1)

The present invention also provides a process for producing a compound represented by formula (1):

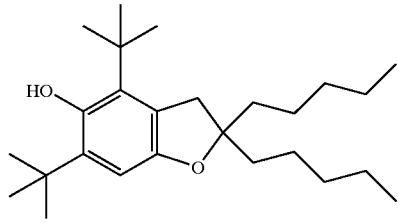
(1)

which comprises the first step of formulating a compound represented by formula (2):

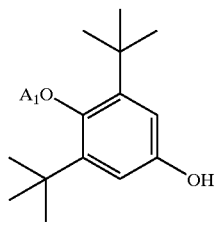
(2)

(where $A_1$ is a protective group) to give a compound represented by formula (3):

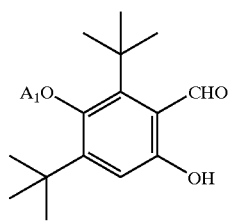
(3)

(where $A_1$ is a protective group), the second step of recrystallizing the compound of formula (3) in a lower alcohol/water mixed solvent to give a purified form of the compound of formula (3), the third step of reacting the compound of formula (3) with a metal hydride and thereafter reacting the same with a compound represented by formula (4):

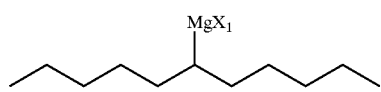
(4)

(where $X_1$ is a halogen atom) to give a compound represented by formula (5):

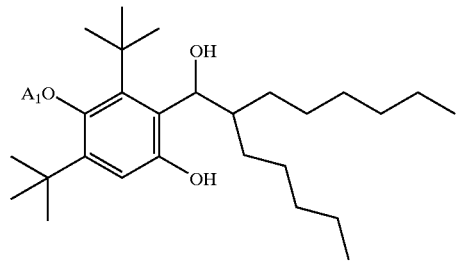
(5)

(where $A_1$ is a protective group), the fourth step of recrystallizing the compound of formula (5) in a hydrocarbon or in a lower alcohol/water mixed solvent to give a purified form of the compound of formula (5), the fifth step of cyclizing the compound of formula (5) to give a compound represented by formula (6):

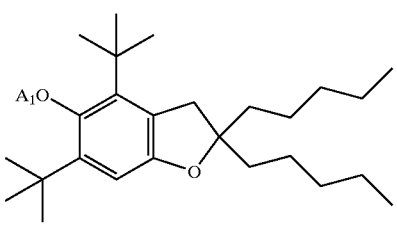
(6)

(where $A_1$ is a protective group), the sixth step of treating the compound of formula (6) with an alkali in a lower alcohol and thereafter treating the same with aluminum oxide to give a purified form of the compound of formula (6), and the seventh step of deprotecting the compound of formula (6) to give a compound represented by formula (1):

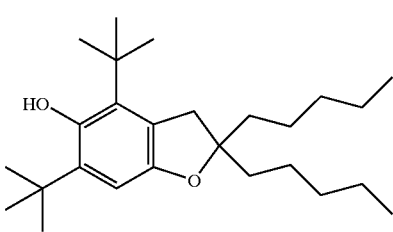
(1)

In addition, the present invention provides a process comprising the fifteenth step of treating a compound of formula (12):

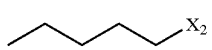
(12)

(where $X_2$ is a halogen atom) with magnesium in diethyl ether or tetrahydrofuran to give a compound represented by formula (13):

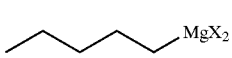
(13)

(where $X_2$ is a halogen atom) and treating the obtained compound with a formic acid ester to give a compound represented by formula (14):

(14)

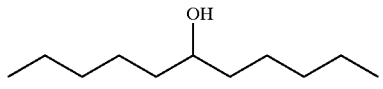

treating the obtained compound with methanesulfonyl chloride or p-toluenesulfonyl chloride to give a compound represented by formula (15):

(15)

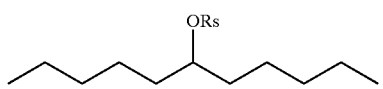

(where $R_s$ is a methanesulfonyl group or a p-toluenesulfonyl group), treating the obtained compound with a halogenating agent so that it is halogenated to give a compound represented by formula (16):

(16)

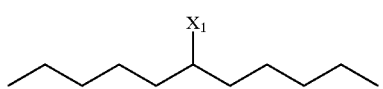

(where $X_1$ is a halogen atom), and treating the obtained compound with magnesium to give a compound represented by formula (4):

(4)

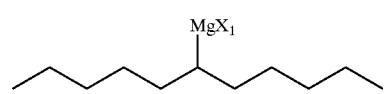

(where $X_1$ is a halogen atom).

The present invention also provides a process comprising the steps of treating a compound of formula (2):

(2)

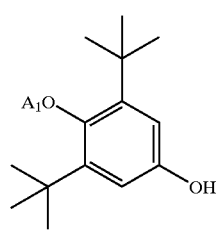

(where $A_1$ is a protective group) with hexamethylenetetramine in the presence of an acid catalyst and thereafter hydrolyzing the same to produce a compound represented by formula (3):

(3)

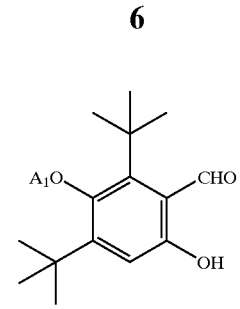

(where $A_1$ is a protective group).

The present invention further provides a process comprising the steps of treating a compound of formula (9):

(9)

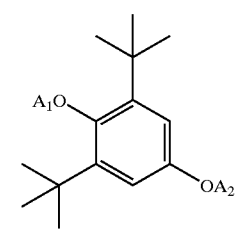

(where $A_1$ and $A_2$ are each a protective group) with hexamethylenetetramine in the presence of an acid catalyst and thereafter hydrolyzing the same to produce a compound represented by formula (3):

(3)

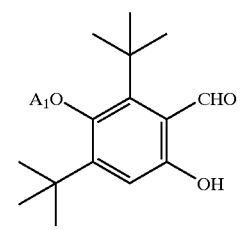

(where $A_1$ is a protective group).

In addition, the present invention provides a process comprising the steps of reacting a compound of formula (3):

(3)

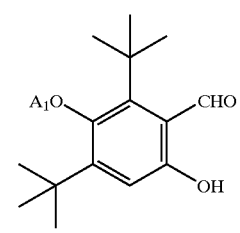

(where $A_1$ is a protective group) with a metal hydride and thereafter reacting the same with a compound of formula (4):

(4)

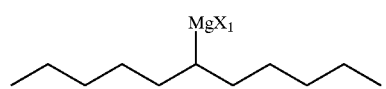

(where X₁ is a halogen atom) to give a compound represented by formula (5):

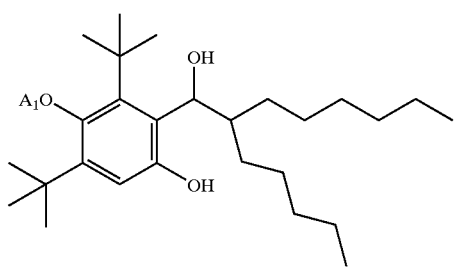

(5)

(where A₁ is a protective group), and recrystallizing the obtained compound of formula (5) in a hydrocarbon or in a lower alcohol/water mixed solvent to give a purified form of the compound of formula (5).

Further in addition, the present invention provides a process comprising the steps of cyclizing a compound represented by formula (5):

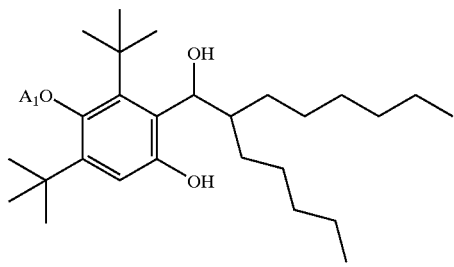

(5)

(where A₁ is a protective group) to give a compound represented by formula (6):

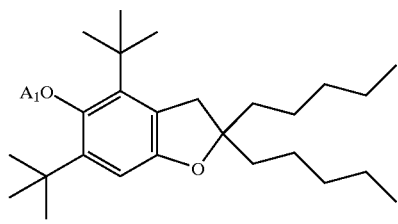

(6)

(where A₁ is a protective group), treating the obtained compound of formula (6) with an alkali in a lower alcohol and treating the same with aluminum oxide to give a purified form of the compound of formula (6).

The present invention also provides a process for producing a compound represented by formula (1):

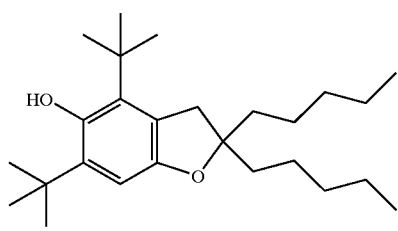

(1)

which comprises the fourteenth step of treating a compound of formula (9):

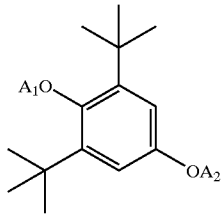

(9)

(where A₁ and A₂ are each a protective group) with hexamethylenetetramine in the presence of an acid catalyst and thereafter hydrolyzing the same to give a compound represented by formula (3):

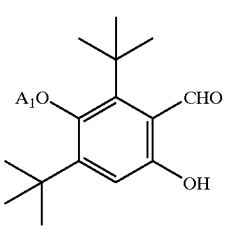

(3)

(where A₁ is a protective group), the third step of reacting the compound of formula (3) with a metal hydride and thereafter reacting the same with a compound represented by formula (4):

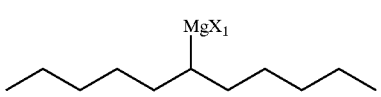

(4)

(where X₁ is a halogen atom) to give a compound represented by formula (5):

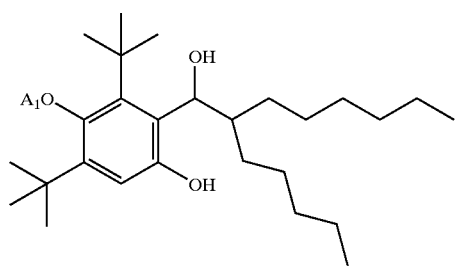

(5)

(where A₁ is a protective group), the fifth step of cyclizing the compound of formula (5) to give a compound represented by formula (6):

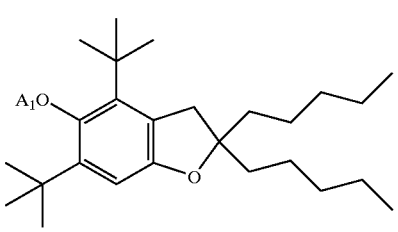

(6)

(where A₁ is a protective group), and the seventh step of deprotecting the compound of formula (6):

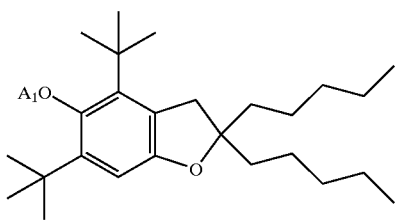
(6)

(where $A_1$ is a protective group) to give a compound represented by formula (1):

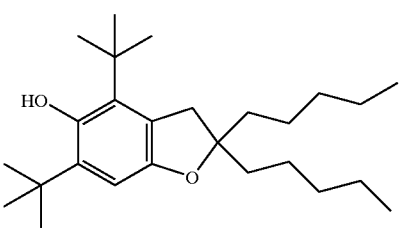
(1)

In addition, the present invention provides a process for producing a compound represented by formula (1):

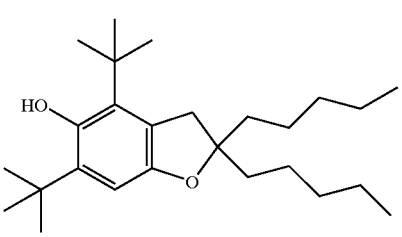
(1)

which comprises the fourteenth step of treating a compound of formula (9):

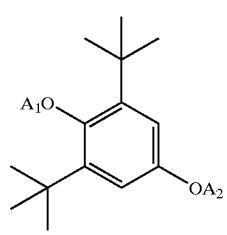
(9)

(where $A_1$ and $A_2$ are each a protective group) with hexamethylenetetramine in the presence of an acid catalyst and thereafter hydrolyzing the same to give a compound represented by formula (3):

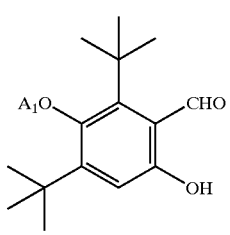
(3)

(where $A_1$ is a protective group), the second step of recrystallizing the compound of formula (3) in a lower alcohol/water mixed solvent to give a purified form of the compound of formula (3), the third step of reacting the compound of formula (3) with a metal hydride and thereafter reacting the same with a compound represented by formula (4):

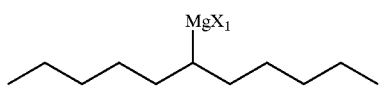
(4)

(where $X_1$ is a halogen atom) to give a compound represented by formula (5):

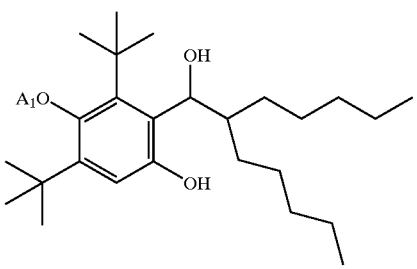
(5)

(where $A_1$ is a protective group), the fourth step of recrystallizing the compound of formula (5) in a hydrocarbon or in a lower alcohol/water mixed solvent to give a purified form of the compound of formula (5), the fifth step of cyclizing the compound of formula (5) to give a compound represented by formula (6):

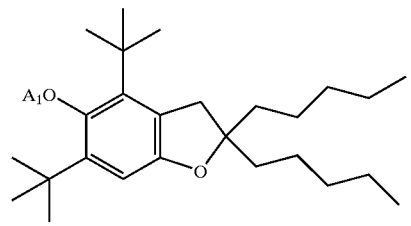
(6)

(where $A_1$ is a protective group), the sixth step of treating the compound of formula (6) with an alkali in a lower alcohol and thereafter treating the same with aluminum oxide to give a purified form of the compound of formula (6), and the seventh step of deprotecting the compound of formula (6):

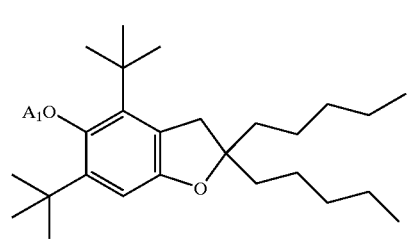
(6)

(where $A_1$ is a protective group) to give a compound represented by formula (1):

(1)

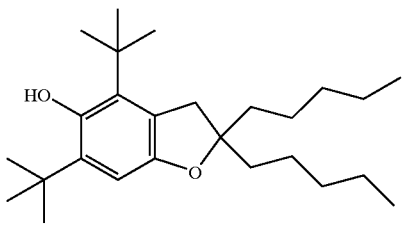

BEST MODE FOR CARRYING OUT THE INVENTION

The following terms as used in the present invention embrace the following meanings unless otherwise specified.

In the present invention, the term "lower" refers to the presence of 1 to 4 carbon atoms and the lower alcohol, for example, means aliphatic alcohols having 1 to 4 carbon atoms and the lower acyl group means acyl groups having 1 to 4 carbon atoms. The term "X times the weight of a substance" refers to the weight ratio per weight of the substance. For example, "two times the weight of a substance" means two weights per weight of the substance.

Examples of the lower acyl group include a formyl group, an acetyl group, a propionyl group, a butyryl group and an isobutyryl group.

Examples of the protective group as $A_1$ and $A_2$ include a lower acyl group, which is preferred; an acetyl group is more preferred.

Exemplary halogenating agents include potassium chloride, lithium chloride, lithium bromide and lithium iodide; potassium chloride and lithium chloride are preferred, with lithium chloride being more preferred.

Examples of the halogen atom as $X_1$ include chlorine, bromine and iodine; chlorine and bromine are preferred, with chlorine being more preferred.

Examples of the halogen atom as $X_2$ include chlorine, bromine and iodine; chlorine and bromine are preferred, with bromine being more preferred.

We next describe the production methods of the invention.

Examples of the production methods of the invention are shown below (method A~method D).

Method A

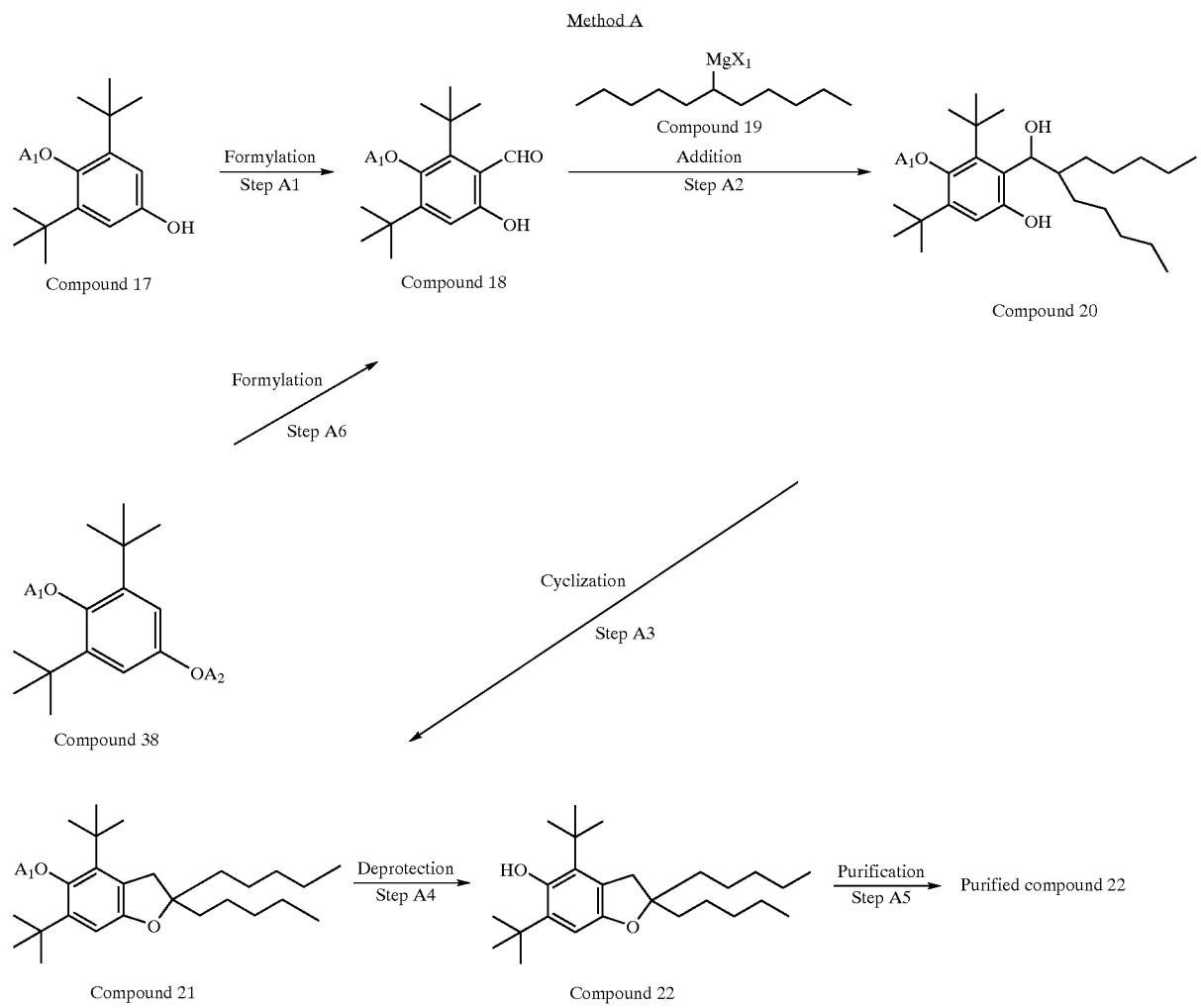

(where $A_1$ and $A_2$ are each a protective group, and $X_1$ is a halogen atom)

Method A is a process in which compound 22 as a compound represented by the above formula (1) or a purified form of compound 22 as a compound represented by the above formula (1) is produced starting from compound 17 as a compound represented by the above formula (2). To begin with, compound 17 as a compound represented by the above formula (2) is formulated to give compound 18 as a compound represented by the above formula (3) (step A1). The formylation can be performed by treatment with hexamethylenetetramine in the presence of an acid catalyst and subsequent hydrolysis.

Examples of the acid catalyst include trifluoroacetic acid and methanesulfonic acid, with methanesulfonic acid being preferred. Any solvents that are inert to the reaction may be employed, as exemplified by acetic acid, trifluoroacetic acid, methanesulfonic acid, a methanesulfonic acid/acetic acid mixed solvent, n-heptane and cyclohexane; acetic acid, trifluoroacetic acid, methanesulfonic acid and a methanesulfonic acid/acetic acid mixed solvent are preferred, trifluoroacetic acid, methanesulfonic acid and a methanesulfonic acid/acetic acid mixed solvent are more preferred, and a methanesulfonic acid/acetic acid mixed solvent is particularly preferred. Hexamethylenetetramine as used in step A1 typically ranges from 1 to 5 equivalents, preferably from 1.5 to 2.5 equivalents, more preferably from 2 to 2.5 equivalents, as relative to compound 17. The reaction temperature typically ranges from 70° C. to 100° C., preferably from 80° C. to 100 ° C., more preferably from 90° C. to 100° C. The reaction time typically ranges from 1 to 6 hours, preferably from 1 to 2 hours. The temperature for hydrolysis typically ranges from 80° C. to 105° C., preferably from 90° C. to 105° C., more preferably from 95° C. to 105° C. The time of hydrolysis typically ranges from 1 hour to 10 hours, preferably from 3 to 8 hours, more preferably from 5 to 7 hours. The obtained compound 18 may be purified if desired but it is preferably purified. A preferred method of purification is recrystallization.

The solvent to be used in recrystallization is preferably a mixture of a lower alcohol such as methanol, ethanol or isopropanol with water, and a mixture of isopropanol and water is more preferred. The ratio of mixing isopropanol with water preferably ranges from 1:1 to 2:1, more preferably from 3:1.8 to 3:2.2. The amount of the solvent to be used in recrystallization preferably ranges from 4 to 8 times the weight of compound 2, more preferably from 4 to 6 times the weight of compound 2. The temperature for recrystallization typically ranges from 0° C. to 30° C., preferably from 0° C. to 20° C. The time of recrystallization typically ranges from 15 minutes to 10 hours, preferably from 0.5 hours to 3 hours.

Compound 18 as a compound represented by the above formula (3) can also be obtained by treating compound 38 as a compound of the above formula (9) with hexamethylenetetramine in the presence of an acid catalyst and thereafter hydrolyzing the same (step A6); this alternative is preferred since it reduces the work load.

Examples of the acid catalyst include trifluoroacetic acid and methanesulfonic acid, with methanesulfonic acid being preferred. Any solvents that are inert to the reaction may be employed, as exemplified by acetic acid, trifluoroacetic acid, methanesulfonic acid, a methanesulfonic acid/acetic acid mixed solvent, n-heptane and cyclohexane; acetic acid, trifluoroacetic acid, methanesulfonic acid and a methanesulfonic acid/acetic acid mixed solvent are preferred, trifluoroacetic acid, methanesulfonic acid and a methanesulfonic acid/acetic acid mixed solvent are more preferred, and methanesulfonic acid is particularly preferred. Hexamethylenetetramine as used in step A6 typically ranges from 1 equivalent to 5 equivalents, preferably from 1.5 equivalents to 2.5 equivalents, more preferably from 2 equivalents to 2.5 equivalents, as relative to compound 38. The reaction temperature typically ranges from 70° C. to 100° C., preferably from 80° C. to 100° C., more preferably from 80° C. to 90° C. The reaction time typically ranges from 1 hour to 6 hours, preferably from 3 hours to 4 hours. The temperature for hydrolysis typically ranges from 80° C. to 105° C., preferably from 90° C. to 105° C., more preferably from 95° C. to 105° C. The time of hydrolysis typically ranges from 1 hour to 10 hours, preferably from 3 hours to 8 hours, more preferably from 5 hours to 7 hours. The obtained compound 18 may be purified if desired but it is preferably purified. A preferred method of purification is recrystallization. The solvent to be used in recrystallization is preferably a mixture of a lower alcohol such as methanol, ethanol or isopropanol with water, and a mixture of isopropanol and water is more preferred. The ratio of mixing isopropanol with water preferably ranges from 1:1 to 2:1, more preferably from 3:1.8 to 3:2.2. The amount of the solvent to be used in recrystallization preferably ranges from 4 to 8 times the weight of compound 2, more preferably from 4 to 6 times the weight of compound 2. The temperature for recrystallization typically ranges from 0° C. to 30° C., preferably from 0° C. to 20° C. The time of recrystallization typically ranges from 15 minutes to 10 hours, preferably from 0.5 hours to 3 hours.

Then, compound 18 as a compound represented by the above formula (3) is reacted with compound 19 as a compound represented by the above formula (4) in the presence of a metal hydride to give compound 20 as a compound represented by the above formula (5) (step A2). Examples of the metal hydride include lithium hydride, sodium hydride, potassium hydride and calcium hydride; lithium hydride and sodium hydride are preferred, with sodium hydride being more preferred. Any solvents that are inert to the reaction may be employed, as exemplified by tetrahydrofuran, diethyl ether, dimethoxyethane and toluene; tetrahydrofuran and diethyl ether are preferred, with tetrahydrofuran being more preferred. Compound 19 to be used in step A2 typically ranges from 1 equivalent to 3 equivalents, preferably from 1 equivalent to 2 equivalents, more preferably from 1.2 to 2 equivalents, as relative to compound 18. The reaction temperature typically ranges from 0° C. to 35° C., preferably from 0° C. to 30° C., more preferably from 5° C. to 25° C. The reaction time typically ranges from 1 hour to 5 hours, preferably from 1 hour to 3 hours, more preferably from 2 hours to 3 hours. These procedures give compound 20. The obtained compound 20 may be purified if desired but it is preferably purified. A preferred method of purification is recrystallization. The solvent to be used in recrystallization is preferably a hydrocarbon such as n-hexane or n-heptane, or a mixture of a lower alcohol such as methanol, ethanol or isopropanol with water; n-hexane and n-heptane are more preferred and n-heptane is particularly preferred. The amount of the solvent to be used in recrystallization preferably ranges from 8 to 15 times the weight of compound 20, more preferably from 9 to 12 times the weight of compound 20. The temperature for recrystallization typically ranges from 0° C. to 30° C., preferably from 0° C. to 15° C. The time of recrystallization typically ranges from 1 hour to 10 hours, preferably from 1 hour to 3 hours.

Then, compound 20 as a compound represented by the above formula (5) is treated with an acid for cyclization, then treated with an alkali and subsequently with aluminum oxide to give a purified form of compound 21 as a compound represented by the above formula (6) (step A3).

Examples of the acid include Lewis acids such as boron trifluoride-diethyl ether complex, and protonic acids such as sulfuric acid and p-toluenesulfonic acid; boron trifluoride-diethyl ether complex and p-toluenesulfonic acid are preferred, with boron trifluoride-diethyl ether complex being more preferred. Any solvents that are inert to the reaction may be employed, as exemplified by n-hexane, n-heptane, benzene, toluene, dichloromethane and chloroform; n-hexane, n-heptane and toluene are preferred, n-hexane and n-heptane are more preferred, and n-heptane is particularly preferred. The acid to be used in step A3 typically ranges from 0.01 equivalent to 3 equivalents, preferably from 1.5 equivalents to 2.5 equivalents, more preferably from 1.8 equivalents to 2.2 equivalents, as relative to compound 20. The reaction temperature typically ranges from 20° C. to 50° C., preferably from 20° C. to 40° C., more preferably from 25° C. to 35° C. The reaction time typically ranges from 1 hour to 6 hours, preferably from 2 hours to 4 hours, more preferably from 3 hours to 4 hours.

Examples of the alkali include potassium hydroxide, sodium hydroxide and sodium methoxide; potassium hydroxide, sodium hydroxide and sodium methoxide are preferred, with potassium hydroxide and sodium methoxide being more preferred. Any solvents that are inert to the reaction may be employed, as exemplified by lower alcohols such as methanol and ethanol; lower alcohols are preferred and methanol and ethanol are more preferred, with methanol being particularly preferred. The alkali to be used in step A3 typically ranges from 0.01 equivalent to 0.3 equivalents, preferably from 0.1 equivalent to 0.3 equivalents, more preferably from 0.2 equivalents to 0.3 equivalents, as relative to compound 20. The reaction temperature typically ranges from 0° C. to 50° C., preferably from 10° C. to 40° C. The reaction time typically ranges from 10 minutes to 120 minutes, preferably from 20 minutes to 60 minutes, more preferably from 20 minutes to 40 minutes.

The above procedures give compound 21. If desired, the obtained compound 21 may be treated with an adsorbent and it is preferably treated with an adsorbent. By treating compound 21 with an adsorbent, a compound represented by formula (23):

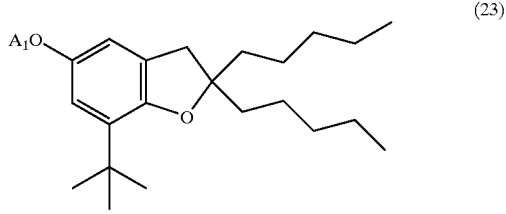

(23)

which is a by-product of the reaction for cyclizing the above compound 20, as well as a compound represented by formula (24):

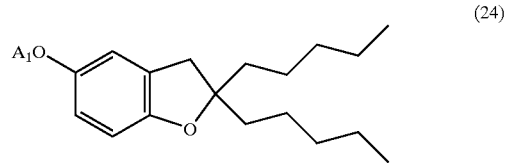

(24)

can be removed to give a purified form of compound 21.

The adsorbent to be used is preferably aluminum oxide. Any solvents that are inert to the reaction may be employed, as exemplified by n-hexane and n-heptane, with n-heptane being preferred. The adsorbent to be used typically ranges from 0.5 to 2 times the weight of compound 20, preferably from 0.8 to 1.5 times the weight of compound 20, more preferably from 0.8 to 1.2 times the weight of compound 20. The reaction temperature typically ranges from 0° C. to 50° C., preferably from 20° C. to 30° C. The reaction time typically ranges from 10 minutes to 60 minutes, preferably from 20 minutes to 40 minutes, more preferably from 25 minutes to 35 minutes.

Next, compound 21 as a compound represented by the above formula (6) is deprotected to give compound 22 as a compound represented by the above formula (1) (step A4). Examples of the deprotecting agent to be used in step A4 include n-butyllithium, diisobutyl aluminum hydride, lithium aluminum hydride, potassium hydroxide, sodium hydroxide and potassium tert-butoxide; diisobutyl aluminum hydride, lithium aluminum hydride, potassium hydroxide and potassium tert-butoxide are preferred, with lithium aluminum hydride and potassium hydroxide being more preferred. Any solvents that are inert to the reaction may be employed and examples include ethers such as tetrahydrofuran, diethyl ether and methyl t-butyl ether, alcohols such as 1-propanol and saturated hydrocarbons such as n-heptane; tetrahydrofuran, methyl t-butyl ether, 1-propanol and n-heptane are preferred, with methyl t-butyl ether and 1-propanol being more preferred. If alcohols are to be used as the solvent, anhydrous alcohols are preferred. The deprotecting agent to be used in step A4 typically ranges from 1 equivalent to 2 equivalents, preferably from 1 equivalent to 1.5 equivalents, more preferably from 1.1 equivalents to 1.2 equivalents, as relative to compound 21. If potassium hydroxide or sodium hydroxide is to be used as the deprotecting agent, they preferably range from 1 equivalent to 10 equivalents, more preferably from 5 equivalents to 7 equivalents, as relative to compound 21. If ethers are to be used as the solvent, the reaction temperature typically ranges from 0° C. to 60° C., preferably from 30° C. to 55° C., more preferably from 45° C. to 55° C. If alcohols are used as the solvent, the reaction temperature is preferably near the boiling point of the solvent and it is more preferred to carry out the reaction under refluxing conditions. The reaction time typically ranges from 30 minutes to 5 hours, preferably from 1 hour to 3 hours, more preferably from 2 hours to 3 hours.

If potassium hydroxide or sodium hydroxide is used as the deprotecting agent, anhydrous alcohols are preferred as the solvent, with anhydrous 1-propanol being more preferred. If potassium hydroxide or sodium hydroxide is used as the deprotecting agent, it is particularly preferred to use anhydrous alcohols as the solvent and carry out the reaction under refluxing conditions. If potassium tert-butoxide is used as the deprotecting agent, it is preferred to use n-heptane as the solvent and carry out the reaction under refluxing conditions. These procedures give compound 22, which may optionally be purified by the following procedures; it is preferred to purify compound 22.

Compound 22 as a compound represented by the above formula (1) is purified by molecular distillation (step A5). Molecular distillation can be performed by known methods.

Compound 19 which is used in the above-described method of production as a compound represented by formula (4) is preferably prepared by method D of the invention.

Compound 38 which is used in the above-described method of production as a compound represented by formula (9) is preferably prepared by method B of the invention.

Compound 17 which is used in the above-described method of production as a compound represented by formula (2) is preferably prepared by method B or C of the invention.

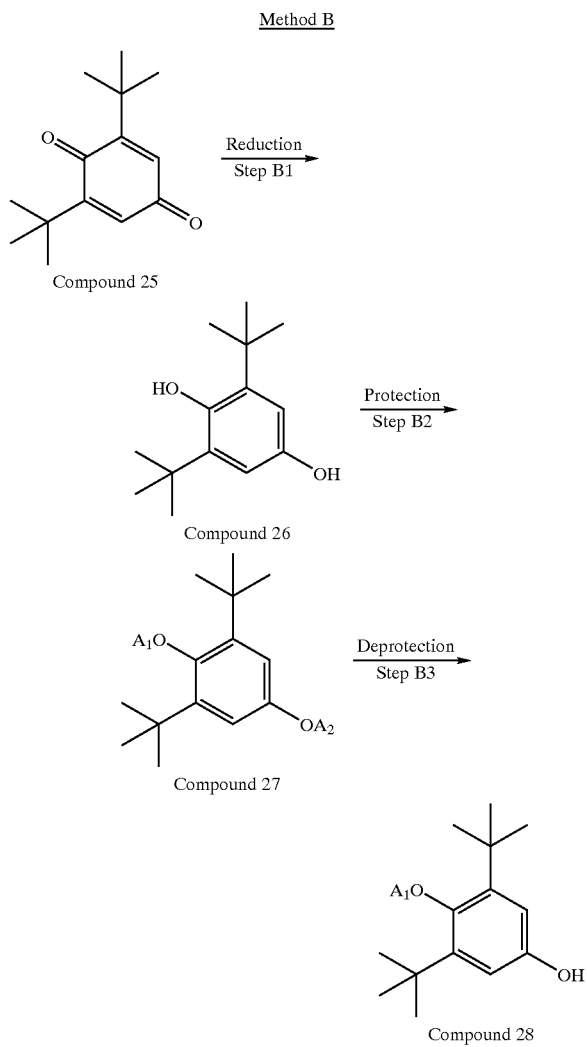

(where $A_1$ and $A_2$ are each a protective group)

Method B is a process in which compound 27 as a compound represented by formula (9) and compound 28 as a compound represented by the above formula (2) are produced starting from compound 25 as a compound represented by formula (7).

To begin with, compound 25 as a compound represented by formula (7) is reduced to give compound 26 as a compound represented by formula (8) (step B1). Examples of the method for reduction that can be employed in step B1 include a method that uses sodium hydrosulfite and a method that involves catalytic reduction with hydrogen, and the use of sodium hydrosulfite is preferred. If the use of sodium hydrosulfite is adopted as a method of reduction, any solvents that are inert to the reaction may be employed, as exemplified by n-hexane, cyclohexane, toluene and an ethyl acetate/water mixed solvent, with cyclohexane and an ethyl acetate/water mixed solvent being preferred. A phase transfer catalyst may be used in step B1 and it is preferred to use a phase transfer catalyst. A preferred phase transfer catalyst is benzyltriethylammonium chloride. The reducing agent to be used in step B1 typically ranges from 1 equivalent to 3 equivalents, preferably from 1 equivalent to 2.5 equivalents, more preferably from 1.2 equivalents to 2 equivalents, as relative to compound 25. The reaction temperature typically ranges from 0° C. to 50° C., preferably from 10° C. to 50° C., more preferably from 20° C. to 40° C. The reaction time typically ranges from 0.5 hours to 3 hours, preferably from 0.5 hours to 3 hours, more preferably from 1 hour to 2 hours.

Then, compound 26 as a compound represented by formula (8) is treated with an acylating agent in the presence of an acid catalyst to protect the hydroxyl groups, thereby giving compound 27 as a compound represented by formula (9) (step B2). Examples of the acylating agent that are used in step B2 include acetyl chloride and acetic anhydride, with acetic anhydride being preferred. Any solvents that are inert to the reaction may be employed, as exemplified by n-hexane, cyclohexane and toluene, with n-hexane and cyclohexane being preferred. Exemplary methods of treatment with an acylating agent include the use of a conc. sulfuric acid catalyst and the reaction with 4-dimethylaminopyridine, followed by the use of a conc. sulfuric acid catalyst; particularly preferred is a method involving the reaction with 4-dimethylaminopyridine, followed by the use of a conc. sulfuric acid catalyst. The acylating agent to be used in step B2 typically ranges from 2 equivalents to 5 equivalents, preferably from 2.5 equivalents to 3 equivalents, as relative to compound 26. The reaction temperature typically ranges from 0° C. to 80° C., preferably from 20° C. to 60° C., more preferably from 45° C. to 55° C. The reaction time typically ranges from 0.5 hours to 6 hours, preferably from 2.5 hours to 4 hours.

From the viewpoint of reducing the work load and cost, it is preferred to use the same solvent in steps B1 and B2. If the same solvent is to be used in steps B1 and B2, cyclohexane may be mentioned as an example and it is preferred to use cyclohexane.

Then, compound 27 as a compound represented by formula (9) is deprotected to give compound 28 as a compound represented by the above formula (2) (step B3). Examples of the deprotecting agent that may be used in step B3 include sodium hydroxide and potassium hydroxide, with sodium hydroxide being preferred. Any solvents that are inert to the reaction may be employed, as exemplified by methanol and a methanol/water mixed solvent, with a methanol/water mixed solvent being preferred. The ratio of mixing methanol with water preferably ranges from 1:1 to 3:2. The deprotecting agent to be used in step B3 typically ranges from 1 equivalent to 1.5 equivalents, preferably from 1.05 equivalents to 1.2 equivalents, as relative to compound 27. The reaction temperature typically ranges from 10° C. to 40° C., preferably from 20° C. to 40° C. The reaction time typically ranges from 0.5 hours to 3 hours, preferably from 1 hour to 2 hours.

Method C

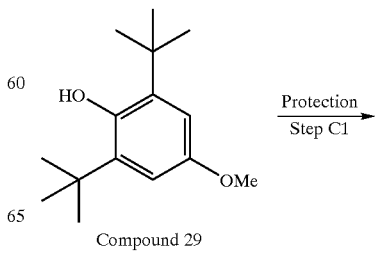

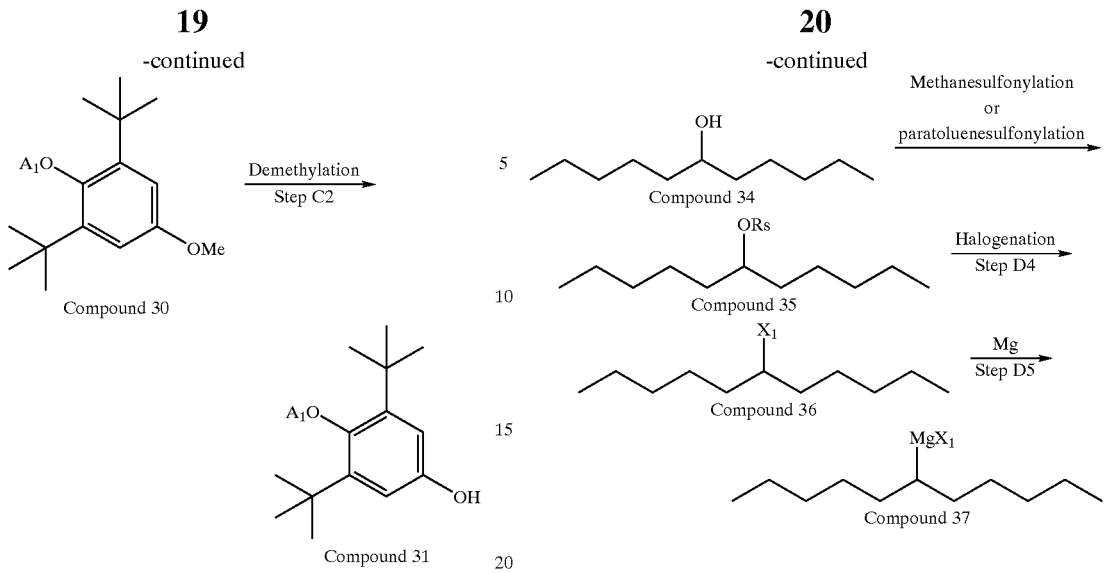

Compound 30

Compound 31

(wherein $A_1$ is a protective group)

Method C is a process in which compound 31 as a compound represented by the above formula (2) is produced starting from compound 29 as a compound represented by formula (10). This process is described in, for example, Japanese Patent Laid-Open No. 206842/1994 and the end compound can be produced by the method described in that patent or by an appropriate modification thereof.

To begin with, compound 29 as a compound represented by formula (10) is treated with an acylating agent in the presence of an acid catalyst to protect the hydroxyl group, thereby giving compound 30 as a compound represented by formula (11) (step C1). Examples of the acylating agent that are used in step C1 include acetyl chloride and acetic anhydride, with acetic anhydride being preferred. Any solvents that are inert to the reaction may be employed, as exemplified by n-hexane, toluene and acetonitrile, with acetonitrile being preferred. Examples of the catalyst include conc. sulfuric acid, with conc. sulfuric acid being preferred. The acylating agent to be used in step C1 typically ranges from 1 equivalent to 10 equivalents, preferably from 1 equivalent to 5 equivalents, more preferably from 1 equivalent to 1.5 equivalents, as relative to compound 29. The reaction temperature typically ranges from 10° C. to 70° C., preferably from 20° C. to 40° C. The reaction time typically ranges from 3 hours to 48 hours, preferably from 5 hours to 12 hours.

Next, compound 30 as a compound represented by formula (11) is demethylated to give compound 31 as a compound represented by the above formula (2) (step C2). An exemplary method of deprotection that may be employed in step C2 is by refluxing in acetonitrile in the presence of both trimethylsilyl chloride and sodium iodide.

Method D

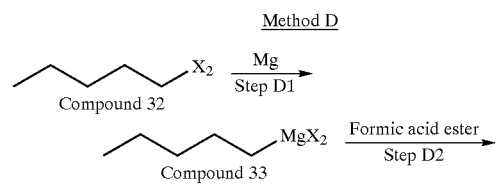

Compound 34

Compound 35

Compound 36

Compound 37

(where $X_1$ and $X_2$ are each a halogen atom; $R_s$ is a methanesulfonyl group or a p-toluenesulfonyl group)

Method D is a process in which compound 37 as a compound represented by the above formula (4) is produced starting from compound 32 as a compound represented by the above formula (12).

To begin with, compound 32 as a compound represented by the above formula (12) is treated with magnesium to give compound 33 as a compound represented by the above formula (13) (step D1). Examples of the magnesium to be used in step D1 include a magnesium powder, a tape of magnesium and chips of magnesium, with a magnesium powder being preferred. Any solvents that are inert to the reaction may be employed, as exemplified by diethyl ether and tetrahydrofuran, with tetrahydrofuran being preferred. The magnesium to be used in step D1 typically ranges from 1 equivalent to 1.5 equivalents, preferably from 1 equivalent to 1.1 equivalents, as relative to compound 32. The reaction temperature typically ranges from 20° C. to 40° C., preferably from 30° C. to 35° C. The reaction time typically ranges from 1 hour to 3 hours, preferably from 1 hour to 2 hours.

Then, compound 33 as a compound represented by the above formula (13) is treated with, for example, a formic acid ester, to give compound 34 as a compound represented by the above formula (14) (step D2). Examples of the formic acid ester to be used in step D2 include methyl formate and ethyl formate, with ethyl formate being preferred. Any solvents that are inert to the reaction may be employed, as exemplified by diethyl ether and tetrahydrofuran, with tetrahydrofuran being preferred. The formic acid ester to be used in step D2 typically ranges from 0.4 equivalents to 0.5 equivalents, preferably from 0.45 equivalents to 0.5 equivalents, as relative to compound 33. The reaction temperature typically ranges from 20° C. to 40° C., preferably from 25° C. to 35° C. The reaction time typically ranges from 1 hour to 3 hours, preferably from 1 hour to 2 hours.

Next, compound 34 as a compound represented by the above formula (14) is treated with a sulfonylating reagent to give compound 35 as a compound represented by the above formula (15) (step D3). Examples of the sulfonylating reagent to be used in step D3 include methanesulfonyl chloride and p-toluenesulfonyl chloride, with methanesulfonyl chloride being preferred. Any solvents that are inert to the reaction may be employed, as exemplified by dichloromethane and pyridine, with pyridine being preferred. The sulfonylating reagent to be used in step D3 typically ranges from 1 equivalent to 2 equivalents, preferably from 1.1 equivalents to 1.5 equivalents, as relative to compound 34. The reaction temperature typically ranges from 0° C. to 30° C., preferably from 10° C. to 30° C. The reaction time typically ranges from 3 hours to 12 hours, preferably from 5 hours to 8 hours.

Next, compound 35 as a compound represented by the above formula (15) is treated with a halogenating agent to give compound 36 as a compound represented by the above formula (16) (step D4). Examples of the halogenating agent that are to be used in step D4 include potassium chloride, lithium chloride, lithium bromide and lithium iodide; potassium chloride and lithium chloride are preferred and lithium chloride is more preferred. Any solvents that are inert to the reaction may be employed, as exemplified by N,N-dimethylformamide and N,N-dimethylacetamide, with N,N-dimethylformamide being preferred. The halogenating agent to be used in step D4 typically ranges from 1 equivalent to 5 equivalents, preferably from 1.2 equivalents to 3 equivalents, more preferably from 1.5 equivalents to 2 equivalents, as relative to compound 35. The reaction temperature typically ranges from 25° C. to 80° C., preferably from 50° C. to 60° C. The reaction time typically ranges from 2 hours to 10 hours, preferably from 3 hours to 5 hours.

Then, compound 36 as a compound represented by the above formula (16) is treated with magnesium to give compound 37 as a compound represented by the above formula (4) (step D5). Examples of the magnesium to be used in step D5 include a magnesium powder, a tape of magnesium and chips of magnesium, with a magnesium powder being preferred. In order to activate magnesium before the reaction, a magnesium activator may be preliminarily reacted with magnesium or it may be mixed with compound 36 before the reaction. Exemplary magnesium activators include iodine and dibromoethane, with dibromoethane being preferred. Any solvents that are inert to the reaction may be employed, as exemplified by tetrahydrofuran and diethyl ether, with tetrahydrofuran being preferred. The magnesium to be used in step D5 typically ranges from 1 equivalent to 2 equivalents, preferably from 1.2 equivalents to 1.5 equivalents, as relative to compound 36. The reaction temperature typically ranges from 25° C. to 40° C., preferably from 30° C. to 40° C. The reaction time typically ranges from 2 hours to 12 hours, preferably from 2 hours to 3 hours.

EXAMPLES

The following examples are provided for further illustrating the present invention but are in no way to be taken as limiting.

Example 1

Synthesis of 5-acetoxy-4,6-di-tert-butyl-2-hydroxybenzaldehyde

To 165 mL of ice-cooled methanesulfonic acid, 53 g (378 mmol) of hexamethylenetetramine was added. To the mixture, 50 g (189 mmol) of 4-acetoxy-3,5-di-tert-butylphenol was added and reaction was performed at 90° C. for 1 hour. The resulting mixture was cooled to 30~40° C. and, after adding 450 mL of water, agitation was effected at 100° C. for 3 hours. The resulting mixture was cooled to 40° C. and extracted twice with 180 mL of 10% ethyl acetate/hexane. The organic layer was washed with 150 mL of a saturated aqueous solution of sodium chloride and the solvent was distilled off under reduced pressure. The residue was dried overnight with a through-flow dryer (parallel flow) at 50° C. to give 39.75 g of the title compound. One half of the title compound was dissolved in 75 mL of isopropanol under heating. The solution was then cooled to 15° C.; after crystal precipitation was confirmed, 50 mL of water was added dropwise. The resulting solution was cooled to 0° C. and agitated for 0.5 hours. The resulting crystal was centrifuged, washed with 50 mL of an isopropanol/water mixed solvent (isopropanol/water=1/1) and dried with a through-flow dryer (parallel flow) at 50° C. for 5 hours to give 16.1 g of 5-acetoxy-4,6-di-tert-butyl-2-hydroxybenzaldehyde.

$^1$H NMR (270 MHz, CDCl$_3$) δ ppm: 1.33(s,9H), 1.52(s, 9H), 2.35(s,3H), 6.93(s,1H), 10.61(s,1H), 12.30(s,1H) IR(cm$^{-1}$): 1758, 1637, 1373, 1211, 1176, 779

Example 2

Synthesis of n-pentylmagnesium bromide

A magnesium powder (102 g, 4.2 mol) was suspended in 1 L of tetrahydrofuran and 500 mL (4.0 mol) of n-pentyl bromide was added dropwise over 6 hours in a nitrogen atmosphere as the internal temperature was kept at 55~60° C. Thereafter, the mixture was agitated at room temperature for 2 hours to prepare a solution of n-pentylmagnesium bromide in tetrahydrofuran.

Example 3

Synthesis of 6-undecanol

To the solution of n-pentylmagnesium bromide in tetrahydrofuran synthesized in Example 2, 162 mL (2.0 mol) of ethyl formate was added dropwise in a nitrogen atmosphere and the mixture was stirred overnight at room temperature. After careful addition of water, the reaction mixture was neutralized with dilute hydrochloric acid and extracted with ethyl acetate. The organic layer was washed with a saturated aqueous solution of sodium chloride, dried over anhydrous magnesium sulfate and thereafter concentrated to give 340.8 g of 6-undecanol.

$^1$H NMR (270 MHz, CDCl$_3$) δ ppm: 0.89(t,6H), 1.22–1.50(m,17H), 3.59(br,1H)

Example 4

Synthesis of 6-methanesulfonyloxyundecane

After dissolving 29.95 g (0.17 mol) of 6-undecanol to 60 mL of pyridine, 29.98 g (0.26 mol) of methanesulfonyl chloride was added dropwise under cooling with ice and the mixture was stirred overnight. Thereafter, 35 mL of 0.5 N aqueous hydrochloric acid was added and the mixture was extracted twice with 200 mL of ethyl acetate. The organic layer was washed with 100 mL of water and a saturated aqueous solution of sodium chloride in that order and thereafter dried over anhydrous magnesium sulfate. After filtering off the magnesium sulfate, the solvent was distilled off to give 44.7 g of 6-methanesulfonyloxy-undecane.

$^1$H NMR (270 MHz, CDCl$_3$) δ ppm: 0.90(t,6H), 1.22–1.48(m,12H), 1.60–1.77(m,4H), 2.99(s,3H), 4.70(m, 1H)

Example 5

Synthesis of 6-chloroundecane

Thirty grams (0.12 mol) of 6-methanesulfonyloxyundecane was dissolved in 150 mL of N,N-dimethylformamide and 15.3 g (0.36 mol) of anhydrous lithium chloride was added to the solution under cooling with ice. The mixture was warmed to 50~55° C. and stirred for 3 hours. Thereafter, the mixture was cooled to 15° C. and 300 mL of cold water was added. The reaction mixture was extracted three times with 150 mL of hexane and the organic layer was sequentially washed with 150 mL of water and 150 mL of a saturated aqueous solution of sodium chloride and thereafter dried over 6 g of anhydrous magnesium sulfate. After filtering off the anhydrous magnesium sulfate, the solvent was distilled off under reduced pressure to give 22.2 g (97.1% in yield) of 6-chloroundecane.

The obtained 6-chloroundecane was distilled under reduced pressure to give 17.3 g (75.7% in yield) of 6-chloroundecane as the main fraction (71° C.~72° C./9–10 mmHg).

$^1$H NMR (270 MHz, CDCl$_3$) δ ppm: 0.90(t,6H), 1.20–1.58(m,12H), 1.62–1.75(m,4H), 3.89(m,1H)

Example 6

Synthesis of 6-undecylmagnesium chloride

In a nitrogen stream, 114 mL of tetrahydrofuran was added to 17.1 g (0.70 mol) of magnesium and the magnesium was activated with 1.1 mL of ethylene bromide. After magnesium activation was confirmed, 111 g (0.58 mol) of 6-chloroundecane and 8.7 mL of ethylene bromide in 1030 mL of tetrahydrofuran were added dropwise (over 1 hour) and after the addition, the mixture was stirred overnight to give a solution of 6-undecylmagnesium chloride in tetrahydrofuran.

Example 7

Synthesis of 4-acetoxy-3,5-di-tert-butyl-2-(1-hydroxy-2-pentylheptyl)phenol

In a nitrogen atmosphere, 270 mL of tetrahydrofuran was added to 13.0 g (0.33 mol) of 60% sodium hydride under cooling with ice; to the mixture, 94.5 g (0.32 mol) of 5-acetoxy-4,6-di-tert-butyl-2-hydroxybenzaldehyde in 200 mL of tetrahydrofuran was added dropwise and the mixture was stirred for 1 hour at room temperature. Thereafter, the Grignard reagent prepared in Example 6 was added dropwise to the mixture, which was subjected to reaction for 1 hour at room temperature. Under cooling with ice, 1000 mL of a saturated aqueous solution of ammonium chloride was added and the mixture was extracted twice with 1000 mL of ethyl acetate. The organic layer was washed with 1000 mL of a saturated aqueous solution of sodium chloride and dried over anhydrous magnesium sulfate. After filtering off the magnesium sulfate, the filtrate was concentrated and the concentrate was dissolved in 1000 mL of hexane under heating. Thereafter, the solution was slowly cooled down to 0° C. for crystallization and the crystal was separated and dried to give 85.6 g of 4-acetoxy-3,5-di-tert-butyl-2-(1-hydroxy-2-pentylheptyl)phenol.

$^1$H NMR (270 MHz, CDCl$_3$) δ ppm: 0.74(t,3H), 0.91(t, 3H), 0.95–1.63(m,16H), 1.29(s,9H), 1.40(s,9H), 2.12(m, 1H), 2.28(s,3H), 2.50(d,1H), 5.22(dd,1H), 6.77(s,1H), 7.89 (s,1H) IR(cm$^{-1}$): 3493, 1761, 1369, 1190, 908

Example 8

Synthesis of 5-acetoxy-4,6-di-tert-butyl-2,2-dipentyl-2,3-dihydrobenzofuran

To 21 L of hexane, 3 kg of 4-acetoxy-3,5-di-tert-butyl-2-(1-hydroxy-2-pentylheptyl)phenol was added and the mixture was cooled to 10° C. After addition of 1.9 kg of a boron trifluoride-diethyl ether complex, the mixture was stirred at 30° C. for 6 hours. To the mixture, 12 L of 10% aqueous sodium hydrogencarbonate was added and the mixture was subsequently stirred. The aqueous layer was discarded and the organic layer was washed with 12 L of 10% aqueous sodium chloride and left to stand overnight. The solvent was concentrated under reduced pressure and 21 L of methanol was added to the residue to dissolve it; then, 24 g of potassium hydroxide was added and the mixture was stirred for 1 hour at room temperature. Thereafter, the mixture was concentrated under reduced pressure and 21 L of hexane and 12 L of water were added to the residue, followed by stirring of the mixture; then, the aqueous layer was discarded and the organic layer was washed with 10% aqueous sodium chloride. To the organic layer, 1.2 kg of anhydrous magnesium sulfate and 3.0 kg of activated alumina were added and the mixture was stirred for 1 hour. Thereafter, the inorganic matter was filtered off with a metal Nutsche and the solvent was concentrated under reduced pressure to give 2.8 kg (99.8% in purity) of 5-acetoxy-4,6-di-tert-butyl-2,2-dipentyl-2,3-dihydrobenzofuran.

$^1$H NMR (270 MHz, CDCl$_3$) δ ppm: 0.88(t,6H), 1.22–1.39(m,12H), 1.30(s,9H), 1.37(s,9H), 1.55–1.75(m, 4H), 2.29(s,3H), 3.10(d,1H), 3.21(d,1H), 6.72(s,1H) IR(cm$^{-1}$): 1760, 1567, 1365, 1214, 1172, 943

Example 9

Synthesis of 4,6-di-tert-butyl-5-hydroxy-2,2-dipentyl-2,3-dihydrobenzofuran

In an argon atmosphere, 0.27 kg of lithium aluminum hydride was added to 18 L of methyl t-butyl ether and the mixture was heated under reflux for 0.5 hours. The solution was cooled to 30° C. and a solution of 2.8 kg of 5-acetoxy-4,6-di-tert-butyl-2,2-dipentyl-2,3-dihydrobenzofuran in 5 L of methyl t-butyl ether was added dropwise; thereafter, the mixture was stirred for 4.5 hours at 50° C. in an argon atmosphere. The solution was cooled to 10° C. and 1.4 L of a saturated aqueous solution of ammonium chloride was slowly added dropwise. Subsequently, 14 L of 10% aqueous hydrochloric acid was added and the mixture was extracted with 14 L of hexane. The aqueous layer was discarded and the organic layer was washed with 14 L of a saturated aqueous solution of sodium chloride; thereafter, the organic layer was concentrated under reduced pressure and the residue was dissolved in 12.5 L of hexane; 2.5 kg of silica gel was added to the solution which was then stirred for 1 hour. After filtering off the silica gel, the filtrate was concentrated under reduced pressure to give 1.9 kg (99.4% in purity) of 4,6-di-tert-butyl-5-hydroxy-2,2-dipentyl-2,3-dihydrobenzofuran.

$^1$H NMR (270 MHz, CDCl$_3$) δ ppm: 0.88(t,6H), 1.22–1.39(m,12H), 1.40(s,9H), 1.49(s,9H), 1.56–1.68(m, 4H), 3.18(s,2H), 4.66(s,1H), 6.62(s,1H) IR(cm$^{-1}$): 3650, 1614, 1573, 1411, 937, 759

Example 10

Synthesis of 2,6-di-tert-butylhydroquinone

To 60 mL of water, 15.8 g (90.8 mmol) of sodium hydrosulfite, 50 mL of ethyl acetate, 10.0 g (45.5 mmol) of 2,6-di-tert-butyl-1,4-benzoquinone and 1.04 g (4.57 mmol) of benzyltriethylammonium chloride were added and the mixture was stirred for 1 hour at 25° C. The reaction mixture was subjected to liquid-liquid separation and the aqueous layer was discarded. The organic layer was washed with 20 mL of 10% aqueous sodium chloride and the solvent was distilled off under reduced pressure to give 2,6-di-tert-butylhydroquinone.

$^1$H NMR (270 MHz, CDCl$_3$) δ ppm: 1.41(s,18H), 4.46 (s,1H), 4.73(s,1H), 6.68(s,2H)

Example 11

Synthesis of 1,4-diacetoxy-2,6-di-tert-butylbenzene

To the 2,6-di-tert-butylhydroquinone obtained in Example 10, 50 mL of hexane, 13.92 g (136.5 mmol) of acetic anhydride and 0.79 g (8.06 mmol) of sulfuric acid were added and the mixture was stirred for 2 hours at 50° C. The mixture was cooled to 10° C. and after adding 30 mL of water and 10 mL of ethyl acetate, the mixture was stirred overnight. The solution was subjected to liquid-liquid separation and the aqueous layer was discarded; thereafter, the organic layer was washed with 40 mL of 7.5% aqueous sodium hydrogencarbonate and 40 mL of 10% aqueous sodium chloride and the solvent was distilled off under reduced pressure to give 1,4-diacetoxy-2,6-di-tert-butylbenzene.

$^1$H NMR (270 MHz, CDCl$_3$) δ ppm: 1.33(s,18H), 2.28 (s,3H), 2.34(s,3H), 7.03(s,2H)

Example 12

Synthesis of 4-acetoxy-3,5-di-tert-butylphenol

The 1,4-diacetoxy-2,6-di-tert-butylbenzene obtained in Example 11 was dissolved in 60 mL of methanol and the solution was cooled to 20° C.; after adding 3.30 g (50.1 mmol) of potassium hydroxide, the mixture was stirred for 1.5 hours. The mixture was cooled to 10~15° C. and then 30 mL of water and 12.5 mL of 6 N hydrochloric acid were gradually added. The solution was cooled to 5° C. and stirred for 0.5 hours. The crystal was centrifuged, washed with 10 mL of a methanol/water mixed solvent (methanol/water=1/1) and dried with a through-flow dryer (parallel flow) overnight at 50° C. to give 10.97 g of 4-acetoxy-3,5-di-tert-butylphenol (91.4% in yield from the 2,6-di-tert-butyl-1,4-benzoquinone of Example 10).

$^1$H NMR (270 MHz, CDCl$_3$) δ ppm: 1.31(s,18H), 2.33 (s,3H), 4.88(s,1H), 6.76(s,2H)

Example 13

Synthesis of 4-acetoxy-3,5-di-tert-butylanisole

To a solution of 1.50 kg (6.35 mol) of 2,6-di-tert-butyl-4-methoxyphenol and 658 mL (6.98 mol) of acetic anhydride dissolved in 1.2 L of acetonitrile, 3 mL of conc. sulfuric acid was added and the mixture was stirred overnight at room temperature. To the mixture, a great excess of water was added and the resulting solids were filtered and dried. The obtained 4-acetoxy-3,5-di-tert-butylanisole was used in the next reaction without further purification.

Example 14

Synthesis of 4-acetoxy-3,5-di-tert-butylphenol

The 4-acetoxy-3,5-di-tert-butylanisole obtained in Example 13 and 1.37 kg (9.14 mol) of sodium iodide were dissolved in 5.0 L of acetonitrile; thereafter, 1.16 L (9.14 mol) of trimethylsilyl chloride was added dropwise and the mixture was refluxed for 8 hours. Thereafter, the reaction mixture was cooled to room temperature, water was added and the organic layer was separated. The organic layer was washed with an aqueous solution of sodium thiosulfate and aqueous sodium chloride in that order and dried over anhydrous sodium sulfate. The crude product obtained by concentrating the organic layer was recrystallized from an ethanol/water mixed solvent and the crystal was dried to give 1.55 kg of the title compound (92.4% in yield from the 2,6-di-tert-butyl-4-methoxyphenol of Example 13).

$^1$H NMR (270 MHz, CDCl$_3$) δ ppm: 1.31(s,18H), 2.33 (s,3H), 4.88(s,1H), 6.76(s,2H)

Example 15

Synthesis of 2,6-di-tert-butylhydroquinone

To 1.2 L of water, 223.2 g (1.09 mol) of sodium hydrosulfite, 1.0 L of cyclohexane, 200.0 g (908 mmol) of 2,6-di-tert-butyl-1,4-benzoquinone and 20.7 g (90.9 mmol) of benzyltriethylammonium chloride were added and the mixture was stirred for 1 hour at 40° C. The reaction mixture was subjected to liquid-liquid separation and the aqueous layer was discarded. The organic layer was washed with 400 mL of water to give a solution of 2,6-di-tert-butylhydroquinone in cyclohexane.

Example 16

Synthesis of 1,4-diacetoxy-2,6-di-tert-butylbenzene

To the solution of 2,6-di-tert-butylhydroquinone in cyclohexane obtained in Example 15, 83.3 mg (0.68 mmol) of 4-dimethylaminopyridine was added; to the mixture, 278.4 g (2.73 mol) of acetic anhydride was slowly added dropwise at 50° C. and the mixture was stirred for 1 hour. To the reaction mixture, 17.8 g (181 mmol) of sulfuric acid was slowly added dropwise and the mixture was stirred for 1 hour at 50° C. The solution was cooled to 30° C. and 600 mL of water was added; the mixture was subjected to liquid-liquid separation and the aqueous layer was discarded. The organic layer was sequentially washed with 800 mL of 7.5% aqueous sodium hydrogencarbonate and 800 mL of water to give a solution of 1,4-diacetoxy-2,6-di-tert-butylbenzene in cyclohexane.

Example 17

Synthesis of 5-acetoxy-4,6-di-tert-butyl-2-hydroxybenzaldehyde

To 1396 g (14.5 mol) of ice-cooled methanesulfonic acid, 254.6 g (1.82 mol) of hexamethylenetetramine was slowly added. To the mixture, the solution of 1,4-diacetoxy-2,6-di-tert-butylbenzene in cyclohexane obtained in Example 16 was added and after the mixture was stirred for a while, the solvent was distilled off under reduced pressure. The reaction mixture was stirred for 4 hours at 80° C.; then, it was cooled to 25° C. and after adding 2.5 L of water, the mixture was stirred for 6 hours at 90~100° C. or above. The mixture was cooled to 30~40° C. and extracted twice with 1.0 L of 10% ethyl acetate/hexane. The organic layer was washed with 800 mL of water and the solvent was distilled off under reduced pressure. To the residue, 800 mL of isopropanol was added and the mixture was heated to form a solution which was then cooled to 10° C. To the cooled solution, a seed crystal (0.1 g) was added and thereafter, crystal precipitation was confirmed; subsequently, 560 mL of water was slowly added dropwise. The solution was cooled to 0–5° C. and after stirring for 1.5 hours, it was filtered under reduced pressure and the crystal was washed with 560 mL of an isopropanol/water mixed solvent (isopropanol/water=1/1). The resulting crystal was dried for 2.5 hours at 50° C. under reduced pressure (on a rotary evaporator) to give 117.8 g of 5-acetoxy-4,6-di-tert-butyl-2-hydroxybenzaldehyde (44.4% in yield from the 2,6-di-tert-butyl-1,4-benzoquinone of Example 15).

$^1$H NMR (270 MHz, CDCl$_3$) δ ppm: 1.33(s,9H), 1.52(s, 9H), 2.35(s,3H), 6.93(s,1H), 10.61(s,1H), 12.30(s,1H) IR(cm$^{-1}$): 1758, 1637, 1373, 1211, 1176, 779 m.p.: 79.0° C.

Example 18

Synthesis of 5-acetoxy-4,6-di-tert-butyl-2,2-dipentyl-2,3-dihydrobenzofuran

To 350 mL of heptane, 70.0 g (156 mmol) of 4-acetoxy-3,5-di-tert-butyl-2-(1-hydroxy-2-pentylheptyl)phenol was added and the mixture was cooled to 10° C. or below. To the mixture, 44.3 g (312 mmol) of a boron trifluoride/diethyl ether complex was added dropwise at 10° C. or below and the mixture was warmed to 30° C. and stirred for 5.5 hours. The solution was cooled to 10° C. or below and thereafter, 350 mL of 7.5% aqueous sodium hydrogencarbonate was added, followed by stirring. The mixture was subjected to liquid-liquid separation and the organic layer was washed with 280 mL of water; thereafter, 7.8 g (40.4 mmol) of 28% sodium methylate and 28 mL of methanol were added and the mixture was stirred for 0.5 hours at room temperature. To the reaction mixture, 280 mL of water was added, followed by stirring; the aqueous layer was discarded and the organic layer was washed with 280 mL of water. To the organic layer, 28.0 g of anhydrous magnesium sulfate and 70.0 g of activated alumina were sequentially added and the mixture was stirred for 0.5 hours at room temperature. The reaction mixture was filtered and the filtrate was concentrated under reduced pressure; thereafter, 70 mL of 1-propanol was added and the mixture was again concentrated under reduced pressure. To the residue, 70 mL of 1-propanol was added to give a solution of 5-acetoxy-4,6-di-tert-butyl-2,2-dipentyl-2,3-dihydrobenzofuran in 1-propanol.

Example 19

Synthesis of 4,6-di-tert-butyl-5-hydroxy-2,2-dipentyl-2,3-dihydrobenzofuran

In a nitrogen atmosphere, 210 mL of 1-propanol was added to 49.0 g (873 mmol) of potassium hydroxide. The reaction vessel was depressurized and then blown with nitrogen; this procedure was performed three times to effect nitrogen purge. The mixture was heated to 100–120° C.; after the dissolution of potassium hydroxide was confirmed, the solution of 5-acetoxy-4,6-di-tert-butyl-2,2-dipentyl-2,3-dihydrobenzofuran in 1-propanol obtained in Example 18 was added dropwise at 100–120° C. In a nitrogen atmosphere, the mixture was stirred for 2 hours at 100° C. or above; thereafter, the mixture was cooled to 30° C. and 120 mL of 25% aqueous citric acid was slowly added dropwise. Further, 280 mL of heptane was added and the mixture was stirred; thereafter, it was subjected to liquid-liquid separation and the organic layer was sequentially washed with 280 mL of water, 280 mL of 7.5% aqueous sodium hydrogencarbonate and 280 mL of 10% aqueous sodium chloride. To the organic layer, 28.0 g of anhydrous magnesium sulfate was added for drying it, which was then filtered under reduced pressure. The filtrate was concentrated under reduced pressure to give 56.5 g of 4,6-di-tert-butyl-5-hydroxy-2,2-dipentyl-2,3-dihydrobenzofuran (99.4% in purity; 93.2% in yield from the 4-acetoxy-3,5-di-tert-butyl-2-(1-hydroxy-2-pentylheptyl)phenol of Example 18).

$^1$H NMR (270 MHz, CDCl$_3$) δ ppm: 0.88(t,6H), 1.22–1.39(m,12H), 1.40(s,9H), 1.49(s,9H), 1.56–1.68(m, 4H), 3.18(s,2H), 4.66(s,1H), 6.62(s,1H) IR(cm$^{-1}$): 3650, 1614, 1573, 1411, 937, 759

Example 20

Synthesis of 4,6-di-tert-butyl-5-hydroxy-2,2-dipentyl-2,3-dihydrobenzofuran

To 22 mL of heptane, 5-acetoxy-4,6-di-tert-butyl-2,2-dipentyl-2,3-dihydrobenzofuran and 1.68 g (15.0 mmol) of potassium tert-butoxide were added and the interior of the reaction vessel was argon-purged by a process consisting of depressurizing the reaction vessel and blowing it with argon. The mixture was heated on an oil bath at 120° C., refluxed for 2 hours in an argon atmosphere and cooled down to room temperature, followed by adding 30 mL of 10% hydrochloric acid dropwise. Further, the mixture was vigorously agitated for 15 minutes and then left to stand still; the organic layer was subjected to HPLC analysis and the generation of 4,6-di-tert-butyl-5-hydroxy-2,2-dipentyl-2,3-dihydrobenzofuran was confirmed by retention time (99.36% in purity).

INDUSTRIAL APPLICABILITY

In the production method of the present invention, (i) purification in each of the reaction steps necessary for obtaining a purified form of the end product can be accomplished simply by employing recrystallization and an adsorbent without performing column chromatography and (ii) the number of steps can be reduced compared to the conventional production methods. Because of these and other advantages, the production method of the invention is useful as an industrial process.

What is claimed is:

1. A process for producing a compound represented by formula (1):

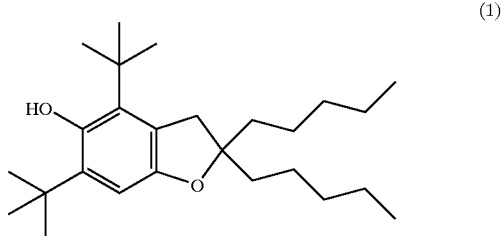

(1)

which comprises the first step of formylating a compound represented by formula (2):

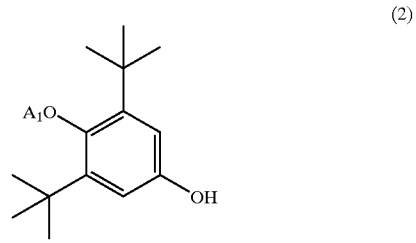

(2)

(where A$_1$ is a protective group) to give a compound represented by formula (3):

which comprises the first step of formulating a compound represented by formula (2):

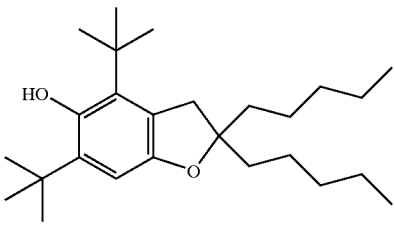
(2)

(where A₁ is a protective group) to give a compound represented by formula (3):

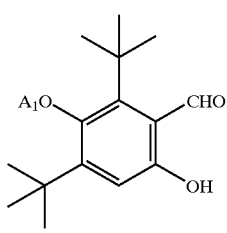
(3)

(where A₁ is a protective group), the second step of recrystallizing the compound of formula (3) in a lower alcohol/water mixed solvent to give a purified form of the compound of formula (3), the third step of reacting the compound of formula (3) with a metal hydride and thereafter reacting the same with a compound represented by formula (4):

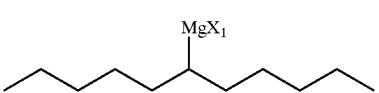
(4)

(where X₁ is a halogen atom) to give a compound represented by formula (5):

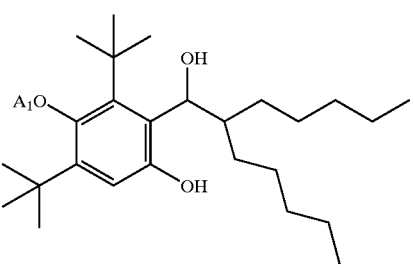
(5)

(where A₁ is a protective group), the fourth step of recrystallizing the compound of formula (5) in a hydrocarbon or in a lower alcohol/water mixed solvent to

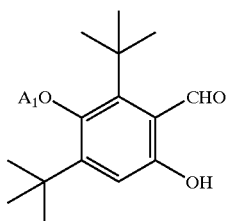
(3)

(where A₁ is a protective group), the third step of reacting the compound of formula (3) with a metal hydride and thereafter reacting the same with a compound represented by formula (4):

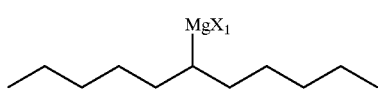
(4)

(where X₁ is a halogen atom) to give a compound represented by formula (5):

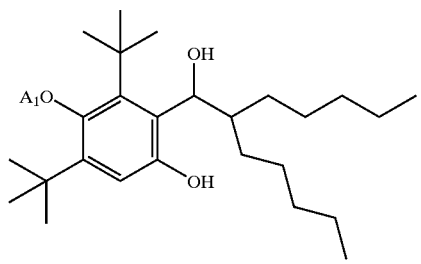
(5)

(where A₁ is a protective group), the fifth step of cyclizing the compound of formula (5) to give a compound represented by formula (6):

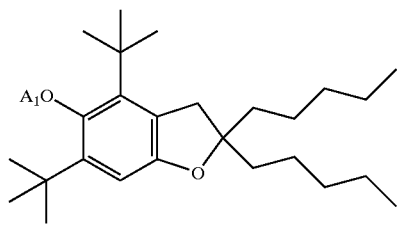
(6)

(where A₁ is a protective group), and the seventh step of deprotecting the compound of formula (6) to give a compound represented by formula (1):

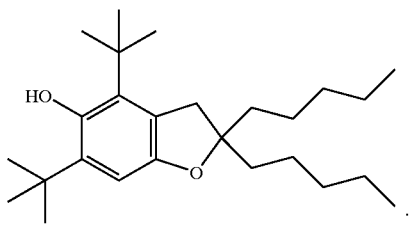
(1)

2. A process for producing a compound represented by formula (1):

give a purified form of the compound of formula (5), the fifth step of cyclizing the compound of formula (5) to give a compound represented by formula (6):

(6)

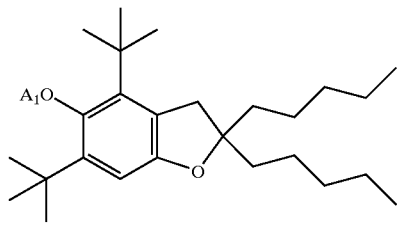

(where $A_1$ is a protective group), the sixth step of treating the compound of formula (6) with an alkali in a lower alcohol and thereafter treating the same with aluminum oxide to give a purified form of the compound of formula (6), and the seventh step of deprotecting the compound of formula (6) to give a compound represented by formula (1):

(1)

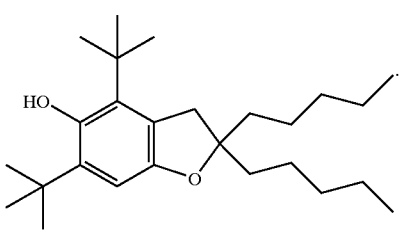

3. The process according to claim 1 or 2, which further includes the eighth step of purifying the compound of formula (1) by molecular distillation after the seventh step.

4. The process according to claim 1 or 2, wherein formulation is performed by treatment with hexamethylenetetramine in the presence of an acid catalyst and subsequent hydrolysis.

5. The process according to claim 1 or 2 for producing a compound represented by formula (1):

(1)

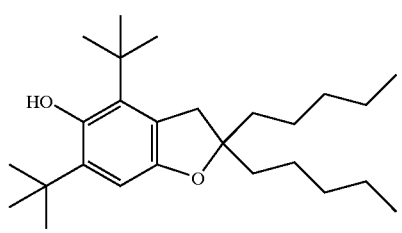

which, prior to the first step, further includes the ninth step of reducing a compound represented by formula (7):

(7)

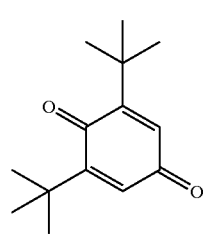

to give a compound represented by formula (8):

(8)

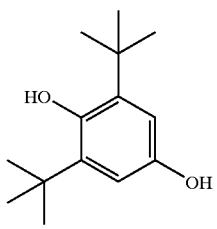

the tenth step of protecting the hydroxyl groups in the compound of formula (8) to give a compound represented by formula (9):

(9)

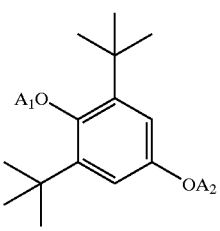

(where $A_1$ and $A_2$ are each a protective group) and the eleventh step of deprotecting the compound of formula (9) to give a compound represented by formula (2):

(2)

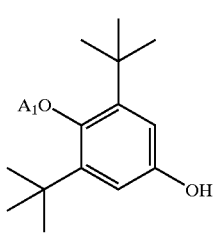

(where $A_1$ is a protective group).

6. The process according to claim 1 or 2 for producing a compound represented by formula (1):

(1)

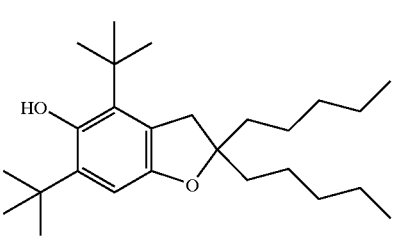

which, prior to the first step, further includes the twelfth step of protecting the hydroxyl group in a compound represented by formula (10):

(10)

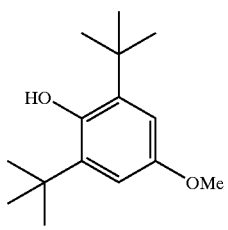

to give a compound represented by formula (11):

(11)

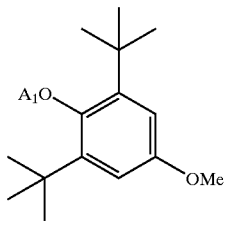

(where A₁ is a protective group) and the thirteenth step of demethylating the compound of formula (11) to give a compound represented by formula (2):

(2)

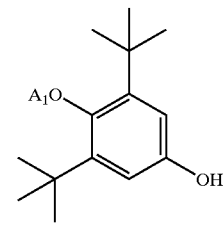

(where A₁ is a protective group).

7. A process comprising the step of treating a compound of formula (12):

(12)

(where X₂ is a halogen atom) with magnesium in diethyl ether or tetrahydrofuran to give a compound represented by formula (13):

(13)

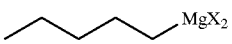

(where X₂ is a halogen atom) and treating the obtained compound with a formic acid ester to give a compound represented by formula (14):

(14)

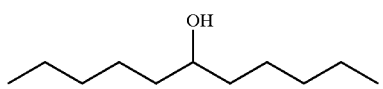

treating the obtained compound with methanesulfonyl chloride or p-toluenesulfonyl chloride to give a compound represented by formula (15):

(15)

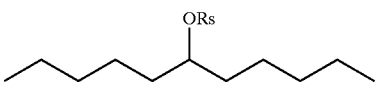

(where $R_s$ is a methanesulfonyl group or a p-toluenesulfonyl group), treating the obtained compound with a halogenating agent so that it is halogenated to give a compound represented by formula (16):

(16)

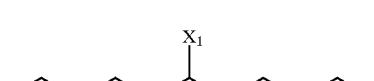

(where X₁ is a halogen atom), and treating the obtained compound with magnesium to give a compound represented by formula (4):

(4)

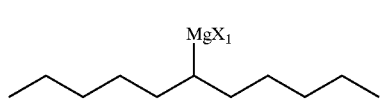

(where X₁ is a halogen atom).

8. A process comprising the steps of treating a compound of formula (2):

(2)

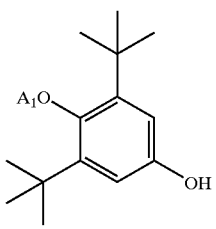

(where A₁ is a protective group) with hexamethylenetetramine in the presence of an acid catalyst and thereafter hydrolyzing the same to produce a compound represented by formula (3):

(3)

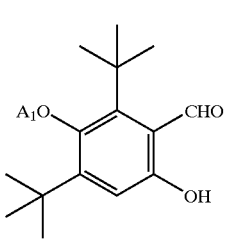

(where A₁ is a protective group).

9. A process comprising the steps of treating a compound of formula (9):

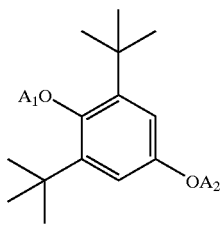
(9)

(where A₁ and A₂ are each a protective group) with hexamethylenetetramine in the presence of an acid catalyst and thereafter hydrolyzing the same to produce a compound represented by formula (3):

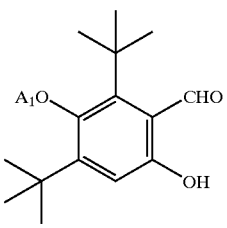
(3)

(where A₁ is a protective group).

10. The process according to claim 8 or 9, which further includes the step of recrystallizing the obtained compound of formula (3) in a solvent comprising a mixture of a lower alcohol and water.

11. A process comprising the steps of reacting a compound of formula (3):

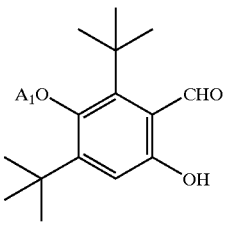
(3)

(where A₁ is a protective group) with a metal hydride and thereafter reacting the same with a compound of formula (4):

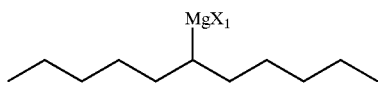
(4)

(where X₁ is a halogen atom) to give a compound represented by formula (5):

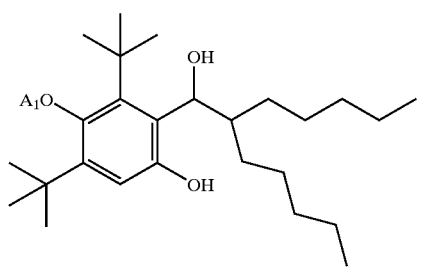
(5)

(where A₁ is a protective group), and recrystallizing the obtained compound of formula (5) in a hydrocarbon or in a lower alcohol/water mixed solvent to give a purified form of the compound of formula (5).

12. A process comprising the steps of cyclizing a compound represented by formula (5):

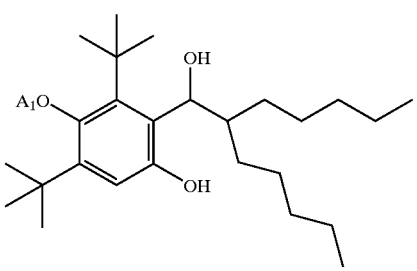
(5)

(where A₁ is a protective group) to give a compound represented by formula (6):

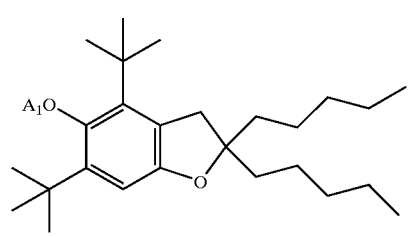
(6)

(where A₁ is a protective group), treating the obtained compound of formula (6) with an alkali in a lower alcohol and treating the same with aluminum oxide to give a purified form of the compound of formula (6).

13. A process for producing a compound represented by formula (1):

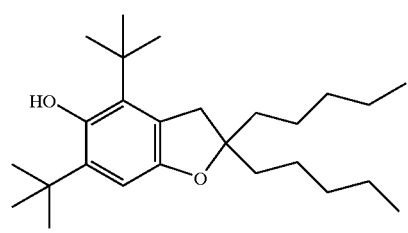
(1)

which comprises the step of treating a compound of formula (9):

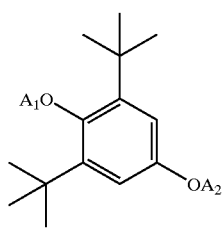
(9)

(where A₁ and A₂ are each a protective group) with hexamethylenetetramine in the presence of an acid catalyst and thereafter hydrolyzing the same to give a compound represented by formula (3):

(3)

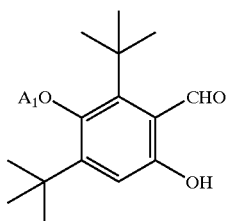

(where $A_1$ is a protective group), the third step of reacting the compound of formula (3) with a metal hydride and thereafter reacting the same with a compound represented by formula (4):

(4)

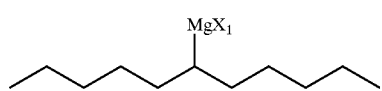

(where $X_1$ is a halogen atom) to give a compound represented by formula (5):

(5)

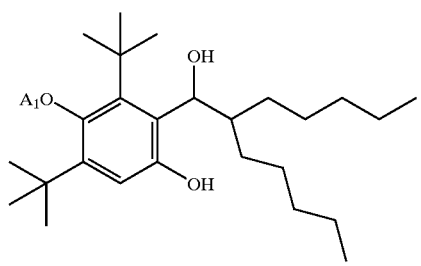

(where $A_1$ is a protective group), the fifth step of cyclizing the compound of formula (5) to give a compound represented by formula (6):

(6)

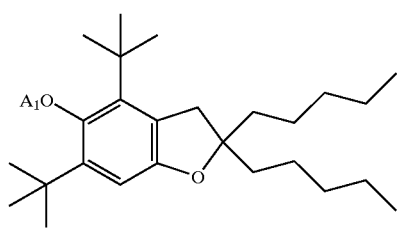

(where $A_1$ is a protective group), and the seventh step of deprotecting the compound of formula (6):

(6)

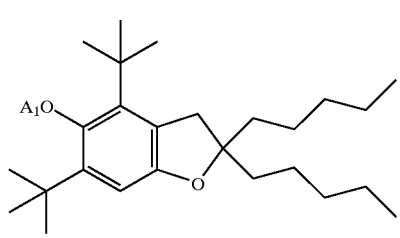

(where $A_1$ is a protective group) to give a compound represented by formula (1):

(1)

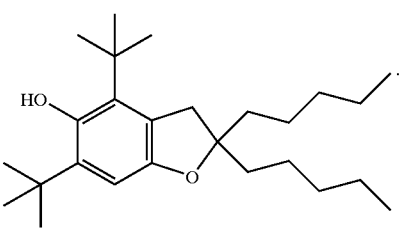

14. A process for producing a compound represented by formula (1):

(1)

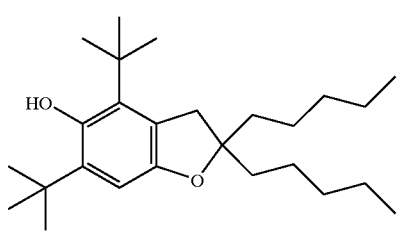

which comprises the step of treating a compound of formula (9):

(9)

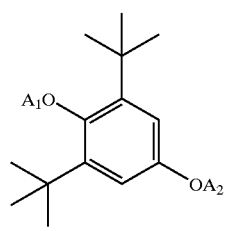

(where $A_1$ and $A_2$ are each a protective group) with hexamethylenetetramine in the presence of an acid catalyst and thereafter hydrolyzing the same to give a compound represented by formula (3):

(3)

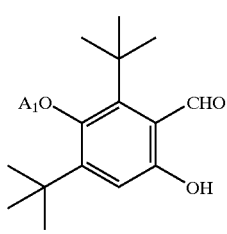

(where $A_1$ is a protective group), the second step of recrystallizing the compound of formula (3) in a lower alcohol/water mixed solvent to give a purified form of the compound of formula (3), the third step of reacting the compound of formula (3) with a metal hydride and thereafter reacting the same with a compound represented by formula (4):

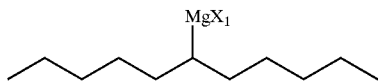
(4)

(where X₁ is a halogen atom) to give a compound represented by formula (5):

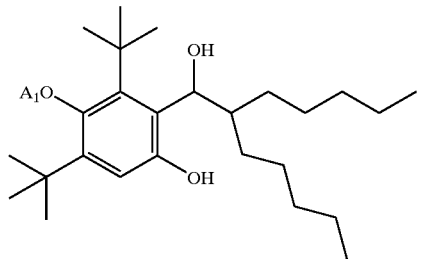
(5)

(where A₁ is a protective group), the fourth step of recrystallizing the compound of formula (5) in a hydrocarbon or in a lower alcohol/water mixed solvent to give a purified form of the compound of formula (5), the fifth step of cyclizing the compound of formula (5) to give a compound represented by formula (6):

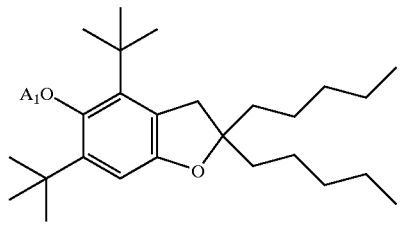
(6)

(where A₁ is a protective group), the sixth step of treating the compound of formula (6) with an alkali in a lower alcohol and thereafter treating the same with aluminum oxide to give a purified form of the compound of formula (6), and the seventh step of deprotecting the compound of formula (6):

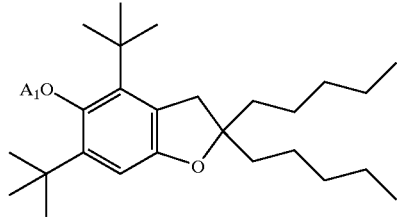
(6)

(where A₁ is a protective group) to give a compound represented by formula (1):

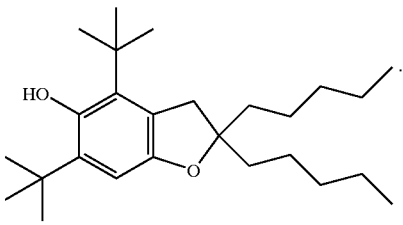
(1)

15. The process according to claim 13 or 14, which further includes the eighth step of purifying the compound of formula (1) by molecular distillation after the seventh step.

16. The process according to claim 13 or 14 for producing a compound represented by formula (1):

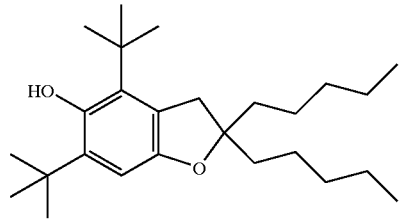
(1)

which, prior to the step of treating formula 9, further includes the step of reducing a compound represented by formula (7):

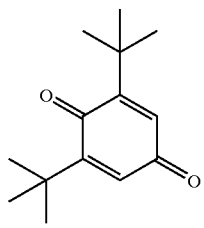
(7)

to give a compound represented by formula (8):

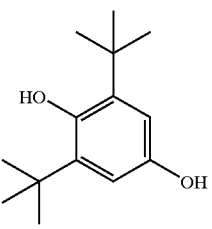
(8)

and the step of protecting the hydroxyl groups in the compound of formula (8) to give a compound represented by formula (9):

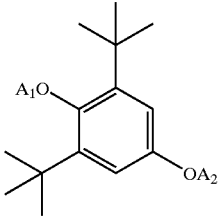
(9)

(where A₁ and A₂ are each a hydroxyl group).

17. The process according to any one of claims 1, 2, 13 or 14 for producing a compound represented by formula (1):

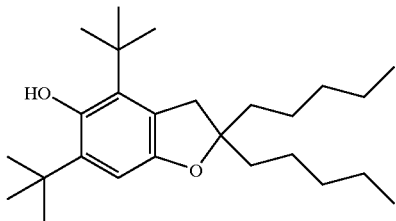
(1)

in which the compound of formula (4) is produced by the process set forth below: a compound represented by formula (12):

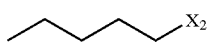
(12)

(where $X_2$ is a halogen atom) is treated with magnesium in diethyl ether or tetrahydrofuran to give a compound represented by formula (13):

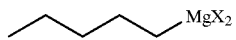
(13)

(where $X_2$ is a halogen atom), the obtained compound is treated with a formic acid ester to give a compound represented by formula (14):

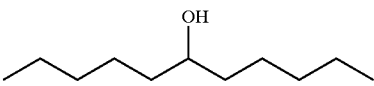
(14)

the obtained compound is treated with methanesulfonyl chloride or p-toluenesulfonyl chloride to give a compound represented by formula (15):

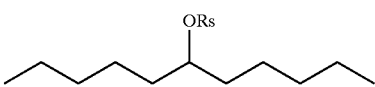
(15)

(where $R_s$ is a methanesulfonyl group or a p-toluenesulfonyl group), the obtained compound is treated with a halogenating agent so that it is halogenated to give a compound represented by formula (16):

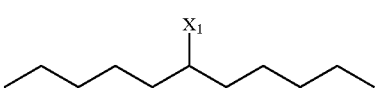
(16)

(where $X_1$ is a halogen atom), and the obtained compound is treated with magnesium to give a compound represented by formula (4):

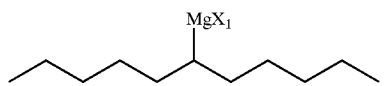
(4)

(where $X_1$ is a halogen atom).

* * * * *